(12) United States Patent
Kumar

(10) Patent No.: US 11,060,129 B2
(45) Date of Patent: Jul. 13, 2021

(54) APTAMER DIGESTION METHOD

(71) Applicant: VICTORIA LINK LIMITED, Wellington (NZ)

(72) Inventor: Shalen Kumar, Lower Hutt (NZ)

(73) Assignee: AURAMER BIO LIMITED, Lower Hutt (NZ)

( * ) Notice: Subject to any disclaimer, the term of this patent is extended or adjusted under 35 U.S.C. 154(b) by 197 days.

(21) Appl. No.: 15/760,981

(22) PCT Filed: Sep. 16, 2016

(86) PCT No.: PCT/NZ2016/050151
§ 371 (c)(1),
(2) Date: Mar. 16, 2018

(87) PCT Pub. No.: WO2017/048138
PCT Pub. Date: Mar. 23, 2017

(65) Prior Publication Data
US 2019/0112634 A1    Apr. 18, 2019

(30) Foreign Application Priority Data

Sep. 18, 2015  (NZ) ........................................ 712485

(51) Int. Cl.
*C12Q 1/6804* (2018.01)
*C12Q 1/6811* (2018.01)
*C12Q 1/6806* (2018.01)
*C12Q 1/6869* (2018.01)

(52) U.S. Cl.
CPC ......... *C12Q 1/6804* (2013.01); *C12Q 1/6806* (2013.01); *C12Q 1/6811* (2013.01); *C12Q 1/6869* (2013.01); *C12N 2310/16* (2013.01)

(58) Field of Classification Search
None
See application file for complete search history.

(56) References Cited

U.S. PATENT DOCUMENTS

| 7,306,904 B2 | 12/2007 | Landegren et al. |
| 7,829,502 B2 | 11/2010 | Lopreato |
| 9,228,207 B2 | 1/2016 | Liu et al. |
| 2011/0251088 A1 | 10/2011 | Lopreato |

FOREIGN PATENT DOCUMENTS

WO    WO-2013025930 A1    2/2013

OTHER PUBLICATIONS

Behera et al., Biopolymers, "Enhanced Deoxyribozyme-Catalyzed RNA Ligation in the Presence of Organic Cosolvents", vol. 99, 382-383 (2012).
Bock et al., Nature, "Selection of single-stranded DNA molecules that bind and inhibit human thrombin", 355(6360): 564-566 (1992).
Dey et al., RNA, "Structural characterization of an anti-gp 120 RNA aptamer that neutralizes R5 strains of HIV-1", vol. 11, 873-884 (2005).
Jo et al., Oligonucleotides , "Development of single-stranded DNA aptamers for specific bisphenol A detection", 21(2):85-91 (2011).
Jost et al., A Laboratory Guide to In Vitro Studies of Protein-DNA Interactions, Birkhauser, Basel, "Exonuclease III Protection Assay for Specific DNA-Binding Proteins", ISBN 978-3-7643-2627-2, pp. 35-43 (1991).
Kelly et al., Journal of Molecular Biology, "Reconciliation of the X-ray and NMR structures of the thrombin-binding aptamer d(GGTTGGTGTGGTTGG)", 256(3):417-422 (1996).
Kim et al., Advances in Biochemical Engineering/Biotechnology, "Advances in aptamer screening and small molecule aptasensors", 140:29-67 (2014).
Kim et al., Biosensors and Bioelectronics, "Electrochemical detection of 17β-estradiol using DNA aptamer immobilized gold electrode chip", 22(11):2525-2531 (2007).
Kulbachinsky, Biochemistry (Moscow), "Methods for selection of aptamers to protein targets", 72(13):1505-1518 (2007).
Luo et al., RNA, "Computational approaches toward the design of pools for the in vitro selection of complex aptamers", 16(11):2252-2262 (2010).
Marshall et al., Methods in Enzymology, "In vitro selection of RNA aptamers", 318:19-214 (2000).
McKeague et al., Journal of Nucleic Acids, "Challenges and opportunities for small molecule aptamer development", 2012:20 (2012).
Mehta et al., Analytical Chemistry, "Selection and characterization of PCB-binding DNA aptamers", 84(3):1669-1676 (2012).
Niazi et al., Bioorganic & Medicinal Chemistry, "ssDNA aptamers that selectively bind oxytetracycline", 16:1254-1261 (2008).
Ruigrok et al., International Journal of Molecular Sciences, "Characterization of aptamer-protein complexes by X-ray crystallography and alternative approaches", 13(8):10537-10552 (2012).
Wang et al., Journal of the American Chemical Society, "Computational and experimental analyses converge to reveal a coherent yet malleable aptamer structure that controls chemical reactivity", 131(41):14747-14755 (2009).
Zianni et al., Journal of biomolecular techniques, "Identification of the DNA bases of a DNase I footprint by the use of dye primer sequencing on an automated capillary DNA analysis instrument", 17(2):103-113 (2006).
International Search Report for PCT/NZ2016/050151 dated Nov. 7, 2016.
Written Opinion for PCT/NZ2016/050151 dated Nov. 7, 2016.

*Primary Examiner* — Tracy Vivlemore
(74) *Attorney, Agent, or Firm* — Marshall, Gerstein & Borun LLP

(57) ABSTRACT

This invention relates to methods of preparing nucleic acid aptamers having selectivity for target substrates. In particular the present invention provides for a method of identifying a ligand binding domain (LBD) in an aptamer by providing a first incubation solution by incubating an aptamer with a target substrate in a first appropriate solvent; and adding an exonuclease enzyme to the first incubation solution to form a second incubation solution in a second appropriate solvent and incubating the second incubation solution, wherein the exonuclease enzyme digests aptamer and provides an aptamer comprising the ligand binding domain.

12 Claims, 9 Drawing Sheets

Specification includes a Sequence Listing.

Figure 6

```
R12C1   --------------TA----GCCTTTAAACTT-GTATGG-GGATTTA
R12C3   ----------CATTTGT-GCCTATGATCT--ATTTCC-GGAT---
R12C6   ----------CAATATGT-G-CA-TGTTTTT--TTGTTT-GAT---
R18C1   GGGATGCCG---TTTGGGCCCAA-GTTCGGCATAGTGTGG-TG--
R18C2   ----------GGTCAGGGGCCAAAGT-GAG---TGTG--GCTGG-
```

Figure 7

| LBD | $E_2$ (nmoles) | | | | | | | EtOH |
|---|---|---|---|---|---|---|---|---|
| | 1200 | 600 | 300 | 150 | 75 | 37.5 | 18.75 | |
| R18 C1 | ● | ● | ● | ● | ● | ● | ● | |
| Ctrl | | | | | | | | |

Figure 11

```
BPA-01    -AAGG-GCACT----CCCCTGTGAT------
BPA-04    TCATGAGCCCGCTT-CCCC------------
BPA-10    TACAGTTCA-T-TTCACCCTGAGAGTGGGCT
```

Figure 12

| LBD | BPA (nmoles) | | | | | | EtOH |
|---|---|---|---|---|---|---|---|
|  | 1200 | 600 | 300 | 150 | 75 | 37.5 |  |
| BPA-04 | ● | ● | ● | ● | ● | ● |  |
| Ctrl |  |  |  |  |  |  |  |

APTAMER DIGESTION METHOD

CROSS REFERENCE TO RELATED APPLICATIONS AND INCORPORATION BY REFERENCE

This application is a U.S. National Stage of International Application No. PCT/NZ2016/050151, filed Sep. 16, 2016, which claims the benefit of New Zealand Patent Application No. 712485, filed Sep. 18, 2015, all of which are hereby incorporated by reference in their entirety.

BACKGROUND OF THE INVENTION

Single-stranded polynucleotide sequences (aptamers) can be generated to bind to ligands that differ widely in molecular size, structure and function. The association of an aptamer with its target substrate is due to a specific nucleotide sequence (the ligand binding domain (LBD)) within the polynucleotide making contact with the target substrate and forming a binding interaction. The number of nucleotides involved directly in this binding interaction is often dependent on the molecular size of the target as well as the nucleotide sequence which is often generated by the SELEX preparation procedure (Kulbachinsky 2007; McKeague and DeRosa 2012; Kim and Gu 2014).

Target substrates that are larger than the polynucleotide sequences (aptamers) offer a large surface area for interaction between the aptamer and the target substrate. Such that most, if not all, of the nucleotides of the polynucleotide sequence can interact with the target substrate. Conversely, target substrates that are smaller than the aptamer are likely to interact with only some of the nucleotides of the polynucleotide sequence. Thus, some of the nucleotides in the polynucleotide sequence can be considered "redundant" (Bock, Griffin et al. 1992; Marshall and Ellington 2000).

Traditionally, methods such as computational modelling (Wang, Hoy et al. 2009; Luo, McKeague et al. 2010), X-ray crystallography (Ruigrok, Levisson et al. 2012), DNA footprinting (Zianni, Tessanne et al. 2006), and NMR (Kelly, Feigon et al. 1996) are used to investigate the structures of aptamers or nucleotides involved in the association with target substrates. All of these methods have been used with aptamers interacting with proteins as the target substrate. In recent years, there have been an increased number of reports of aptamers targeting low molecular weight target substrates such as steroids (Kim, Jung et al. 2007; Jo, Ahn et al. 2011; Mehta, Rouah-Martin et al. 2012). However, progress in deciphering the key nucleotides responsible for specific binding with target substrates has been limited. Enzymes having the ability to excise double stranded DNA (dsDNA) have been widely applied for investigating the interactions of target substrates, such as DNA-binding proteins with their binding sites on DNA. Until recently, knowledge concerning exonuclease activity with respect to the digestion of nucleic acid sequences has been poorly understood.

US 2011/0251088 discloses methods of selecting aptamers susceptible for a particular target substrate based on the susceptibility of the aptamer to digestion by nuclease enzymes. The aptamers that are selected are carried forward in sequential rounds of selection thereby reducing the required number of selection rounds required to find an aptamer that binds strongly to the target substrates.

U.S. Pat. No. 7,306,904 provides assays for detection and/or quantification of soluble target substrates through the use of proximity probes that have a binding moiety with an affinity for the target substrate. The proximity probes comprise a binding moiety and a nucleic acid. The nucleic acid from one proximity probe is only capable of interaction with the nucleic acid from the other proximity probe when these are in close proximity, i.e. have bound to the analytes for which they are specific.

WO 2013025930 relates to nucleic acid aptamer molecules that include a domain that binds to an oestrogen receptor. The aptamers and encoding constructs inhibit oestrogen receptor activity in a cell and are potentially useful in treating oestrogen receptor-positive cancers.

U.S. Ser. No. 14/326,329 relates to RNA-guided nuclease complexes comprising a switchable guide RNA (gRNA) to allow switching "on" or "off" of the nuclease enzyme and is applied to targeted cleavage of a specific sequence within a genome for gene targeting modification in living cells.

RNA and DNA polynucleotide sequences (aptamers) have been applied in a number of therapeutic and sensing platforms since their first development. For example, aptamers have been applied for detecting vascular endothelial growth factor (VEGF165) [Gold, Larry and Craig Tuerk, 2006]; the detection of thrombin [Bock, L. C.; Griffin, L. C.; Latham, J. A.; Vermaas, E. H.; Toole, J. J. 1992; human thrombin (Nature 1992, 355, 564-566.]; oxytetracycline [Niazi, Lee et al. 2008]; and PCB72 and PCB 106 [Mehta, Rouah-Martin et al. 2012].

RNA and DNA polynucleotide sequences such as aptamers are often produced by a process known as SELEX. SELEX is a commonly used technique in the biotechnology field for producing polynucleotide sequences such as aptamers and is often also accompanied by polymerase chain reaction (PCR) to amplify the polynucleotide sequence.

The SELEX process starts with the synthesis of a library of randomly generated polynucleotide sequences. The library of randomly generated polynucleotide sequences are exposed to a target substrate, for example, proteins or small organic compounds, and the randomly generated polynucleotide sequences that fail to bind to the target substrate are removed from the library, usually by affinity chromatography. Conversely, the polynucleotide sequences that are bound to the target substrate are replicated and amplified by PCR so as to prepare for subsequent SELEX rounds. In subsequent SELEX rounds, elution conditions are manipulated to identify polynucleotide sequences with the highest binding affinity for the target substrate.

SELEX produced randomly generated polynucleotide sequences are flanked by nucleotide sequences at the 5' and 3' ends that serve as forward and reverse primers. These primers are strands of short nucleic acid sequences (often about 10 base pairs but the number may vary) but the primers of known sequences that assist with the PCR process and act as a "build-up" starting point for the polynucleotide synthesis. It is generally considered in the art that forward and reverse primer sequences are elements required for nucleic acid replication and amplification only, and that these forward and reverse primer sequences are not involved in binding the target substrate. Consequently, polynucleotides (aptamers) that are utilised in sensing platforms are often refined or modified by eliminating and removing the nucleotide bases of the primer region. Refinements to the polynucleotide sequences (aptamers) such as primer removal and/or reduction to the ligand binding domain are based on software (mFold) predicted 2-dimensional (2D) structures of the polynucleotide sequence. This software approach is not always informative, since the software considers the whole polynucleotide sequence and not the specific LBD. The exact LBD sequence is only theorised and this can result in removal of bases that are important for binding the target substrate.

Furthermore, the number of nucleotides involved in the formation of the LBD may not be the same for every target substrate ligand, but may be dependent on the combination and variation of the nucleotides constituting the entire polynucleotide sequence (aptamer) and the interaction of these nucleotides with the reactive moieties available on the target substrate.

Without specific knowledge of the nucleotide bases that comprise the LBD, refinements achieved by using the software predicted method to identify a LBD are achieved more by chance rather than by a systematic method. Such refinement also affects the applicability on various application platforms.

It is also generally considered in the art that the LBD is found only in the random region of the polynucleotide sequence that is evolved during the SELEX process. However, if there are a set of nucleotide bases (e.g. forward and reverse primers) present that do not change during the SELEX process while the neighbouring region is consistently changing, it cannot be relied upon that those non-changing nucleotides (forward and reverse primers) are redundant and are not required for target substrate binding or stability.

The present inventor has found that the nucleotide bases (e.g. forward and reverse primers) are protected from enzymatic digestion and in some cases, the primers may be an important component of the polynucleotide sequences associated with the process of binding the target substrate. This could be either through a binding interaction with the substrate, or they may even provide a stabilisation effect of the overall polynucleotide sequence, despite not technically binding to the substrates.

Furthermore, methods such as structural modelling analyses, which are also commonly used, are not sufficiently informative for predicting complex secondary structures because of software limitations. The software cannot predict or establish information on the flexibility of the polynucleotide sequence (aptamer). Since the polynucleotide sequences are not stabilised by another complementary strand of a polynucleotide sequence, the specific folding remains unknown.

DNA foot-printing of dsDNA has been known in the art for some time and is a method of identifying dsDNA binding proteins. In DNA foot-printing, there is often a binding cleft in which the dsDNA helix will sit while the enzyme cleaves the dsDNA during protein interaction. This cleavage by the enzyme may or may not occur at the terminal ends of the dsDNA and may result in cleavage at points anywhere along the dsDNA sequence. However, DNA foot-printing cannot be directly extrapolated to single stranded polynucleotide sequences. Single stranded polynucleotide sequences behave in a different manner to dsDNA since single stranded polynucleotide sequences (aptamers) are not stabilised by another polynucleotide sequence. Consequently, the single stranded polynucleotide sequence is far more flexible in nature and its tertiary structure unpredictable.

In order for DNA foot-printing to work efficiently, there also needs to be prior knowledge of the postulated LBD. A specific sequence of nucleotide bases also needs to be inserted into the dsDNA so that that the enzyme can recognise and cleave the dsDNA at a specific location. In addition, prior knowledge is also necessary for labelling the DNA because labels at the site of binding may affect the target and DNA association. The requirement for the use of labels at either the 5' or 3' end (radioactive or fluorescence) can also be a limiting factor since small fragments of sequence need to be able to be visualised. Furthermore, cleavage agents need to be selected with previous knowledge of the dsDNA sequence and the target substrate, and the cleavage agent also needs to be suitable to digest the dsDNA. Therefore, these limitations of DNA foot-printing mean that DNA foot-printing cannot be directly correlated and applied to single stranded polynucleotide sequences (aptamers).

Therefore, there remains a need to provide an efficient method that allows identification of ligand binding domains and the specific nucleic acid sequences that are involved in the binding of target substrates.

It is an object of the present invention to provide a method for identification of a ligand binding domain (LBD) on nucleic acid aptamers or to at least provide the public with a useful alternative.

SUMMARY OF INVENTION

The present inventor has surprisingly and advantageously developed a methodology for identifying the ligand binding domain (LBD) in nucleic acid sequences, particularly those that interact with desirable substrate targets. The present invention provides a more efficient method of preparing nucleic acid aptamers with high selectivity when compared to current methods.

The use of enzymes to identify a single stranded polynucleotide's (aptamer's) LBD has not been shown before and provides the benefit of being less resource demanding when compared to existing techniques such as DNA foot-printing, X-ray crystallography or NMR.

In a first aspect, the present invention provides a method of identifying a ligand binding domain (LBD) in an aptamer, wherein the method comprises:
  providing a first incubation solution by incubating an aptamer with the target substrate in a first appropriate solvent; and
  adding an exonuclease enzyme to the first incubation solution to form a second incubation solution and incubating the second incubation solution in a second appropriate solvent, wherein the exonuclease enzyme digests aptamer and provides a digested aptamer comprising the ligand binding domain.

In a second aspect of the invention is provided a kit when used in a method of identifying a ligand binding domain (LBD) in an aptamer, wherein the kit comprises instructions for:
  providing a first incubation solution by incubating an aptamer with the target substrate in a first appropriate solvent; and
  adding an exonuclease enzyme to the first incubation solution to form a second incubation solution and incubating the second incubation solution in a second appropriate solvent, wherein the exonuclease enzyme digests aptamer and provides a digested aptamer comprising the ligand binding domain.

In an embodiment of any one of the aspects of the invention of any one of the aspects of the invention, the aptamers are selected from ssDNA aptamers and RNA aptamers. Preferably, the aptamers selectively bind or have an affinity for the target substrate.

In an embodiment of any one of the aspects of the invention, the target substrates are smaller in size than the aptamer to which it binds. Preferably, the target substrates are ions, small molecules, amino acids, peptides, proteins and protein derivatives, antibodies, disease markers, bio-markers, active pharmaceutical compounds, derivatives and metabolites of any of the aforementioned.

In an embodiment of any one of the aspects of the invention, the target substrate may also be a pollutant.

Preferably, the target substrates are small molecules. Preferably, the target substrates are small molecules that are selected from chemicals that mimic hormones, hormones, naturally occurring phytoestrogens, narcotics and metabolites thereof. Preferably, the target substrate is an endocrine disrupting compound, a steroidal sex hormone, metabolites or synthetic variants thereof. More preferably, the target substrate is selected from endocrine disrupting compounds, and metabolites thereof. The target substrates may be selected from 17β-oestradiol (E2); oestrone; oestriol; androstenedione; testosterone; dihydrotestosterone; pregnenolone; progesterone; 17α-hydroxyprogesterone, 17α-ethynylestradiol; isoflavones; lignans; coumestans; organohalides including organochlorines, polychlorinated organic compounds, polychlorobiphenyl (PCB); alkylphenols; alkylphenol ethoxylates; phthalates; bisphenol-A (BPA); Bis (4-hydroxyphenyl) methane; cholesterol; adenosine; triclosan; or synthetic steroids such as diethylstilboestrol (DES); cocaine, heroin and any metabolites of the mentioned compounds thereof. More preferably, the target substrate is selected from 17β-oestradiol, testosterone, progesterone, adenosine and BPA.

The target substrate may also be hormone or a marker of a condition of disease in a body, known markers of disease, for example overexpression of a cancer gene to detect cancer, detection of molecules or markers associated with infection, or to establish levels of specific metabolites associated with a particular condition.

In another embodiment of any one of the aspects of the invention, the aptamer is optionally denatured prior to formation of the first incubation solution. Preferably, the aptamer is denatured by heat. Alternatively, the aptamer can be pre-incubated without denaturing prior to formation of the first incubation solution.

In an embodiment of any one of the aspects of the invention, the first incubation solution is incubated for a long period of time, sufficient for substantial binding of the aptamer and the target substrate. Preferably, the aptamer and target substrate achieve the lowest energy binding conformation. Preferably, the incubation time of the first incubation solution is from about 2 mins to about 18 hours. More preferably, the incubation time of the first incubation solution is from about 2 hours to about 6 hours. Yet most preferably, the incubation time of the first incubation solution is about 4 hours.

Preferably, the first incubation solution is incubated at a temperature of from about 10° C. to about 50° C. More preferably, the first incubation solution is incubated at a temperature of from about 15° C. to about 40° C. Yet even more preferably, first incubation solution is incubated at a temperature of from about room temperature to about 37° C. Most preferably, first incubation solution is incubated at a temperature of about room temperature or ambient temperature (from about 16° C. to about 25° C.).

In an embodiment of any one of the aspects of the invention, the second incubation solution is incubated for a time sufficient for the exonuclease enzyme to digest the aptamer and provide a sequence comprising the ligand binding domain. Preferably the second incubation solution is incubated from about 1 min to about 2 hours. More preferably, the incubation time of the second incubation solution is from about 10 mins to about 1 hour. Yet most preferably, the incubation time of the second incubation solution is about 30 mins.

Preferably, the second incubation solution is incubated at a temperature of from about 5° C. to about 50° C. More preferably, the second incubation solution is incubated at a temperature of from about 15° C. to about 40° C. Most preferably, second incubation solution is incubated at about 37° C.

The second incubation solution may be denatured after the incubation process is complete. The denaturing of the second incubation solution should be sufficient to denature the exonuclease enzyme. A person skilled in the art will readily understand conditions, temperatures and time periods suitable for the denaturing of the exonuclease enzyme.

The appropriate solvent provides optimal aptamer function and is preferably the same solvent that the aptamer will be utilised, generated, or digested in. A person of skill in the art will realise that appropriate solvents may vary between different aptamers.

In an embodiment of any one of the aspects of the invention, the solvents for the first and second incubation solutions are selected from an aqueous solution or a water miscible organic solvent. Preferably, the solvents for the first and second incubation solutions are selected from an aqueous solution or solvent, or combination thereof in which the aptamer will be utilised in or has been generated in. Preferably, the aqueous solution is a buffer solution.

Preferably, the aqueous solution or solvent in which the aptamer will be utilised, generated or digested in further comprises a water miscible organic solvent. Preferably, the buffer solution or solvent in which the aptamer will be utilised, generated or digested in further comprises a water miscible organic solvent. The water miscible organic solvent may be present in an amount suitable to assist with retaining the solubility of the target substrate in the first or second incubation solution. The water miscible solvent may be one water miscible solvent or a mixture of two or more water miscible solvents. The water miscible solvent may be selected from an alcoholic solvent, a ketone solvent, an ether, an amide, a sulfoxide, or a mixture thereof. More preferably, the water miscible organic solvent is selected from selected a from acetone, acetonitrile, dioxane, dimethylsulfoxide (DMSO), N,N-dimethylformamide (DMF), ethanol (EtOH), isopropyl alcohol (IPA), methanol (MeOH) and tetrahydrofuran (THF), or a combination or mixture thereof. Most preferably, the water miscible solvent is ethanol.

Preferably, the water miscible solvent is present in the first incubation solution and/or second incubation solution in an amount of from about 0.5% v/v to about 25% v/v. More preferably the water miscible solvent is present in about 2.5% v/v to about 15% v/v. Most preferably, the water miscible solvent is present in an amount of about 5% v/v.

The solvents for the first and second incubation solutions may be the same or different. Preferably, the first and second incubation solvents are the same.

In yet another embodiment of any one of the aspects of the invention, the exonuclease is selected from a 5' exonuclease and a 3' exonuclease. Suitable, 5' exonucleases include but are not limited to [Lambda exonucleases, T7 Exonuclease, RecJ$_f$. Suitable, 3' exonucleases include but are not limited to Exonuclease T, Exonuclease I. A person of skill in the art will realise that any suitable exonuclease known in the art may be used.

In another embodiment of any one of the aspects of the invention, the aptamer is isolated after enzymatic digestion has taken place. Methods of isolating the LBD aptamer from the reaction solution would be apparent and understood by those of skill in the art. However, methods include but are not limited to concentration, precipitation, ligation into a plasmid, electrophoresis (including gel based or capillary electrophoresis), microfluidic systems and any combination of the aforementioned.

In another embodiment of any one of the aspects of the invention, the isolated aptamer may be amplified. For example, the aptamer could be amplified by PCR; or alternatively, by direct ligation into a plasmid followed by transformation into a vector system. Other methods commonly used in the art that would be understood by a skilled person may also be used.

In a further aspect of the invention is provided sequences identified by the method and any one of the aspects and/or embodiments herein described. Preferably, the sequences are selected from:

```
                                              (SEQ ID No 9)
5'-TAGCCTTTAAACTTGTATGGGGATTTA-3';

(SEQ ID No 10)
5'-CATTTGTGCCTATGATCTATTTCCGGAT-3';

(SEQ ID No 11)
5'-CAATATGTGCATGTTTTTTGTTTGAT-3';

(SEQ ID No 12)
5'-GGGATGCCGTTTGGGCCCAAGTTCGGCATAGTGTGGTG-3';

(SEQ ID No 13)
5'-GGTGAGGGGCCAAAGTGAGTGTGGCTGG-3';

(SEQ ID No 14)
5'-AAGGGCACTCCCCTGTGAT-3';

(SEQ ID No 15)
5'-TCATGAGCCCGCTTCCCC-3';
and (SEQ ID No 16)
5'-TACAGTTCATTTCACCCTGAGAGTGGGCT-3'.
```

Further aspects of the invention, should be considered in all its novel aspects and will be apparent to those skilled in the art upon reading of the following description.

DESCRIPTION OF THE FIGURES

FIG. 6 Alignment of nucleotides forming the E2 LBD. R12C1 (SEQ ID No 9), R12C3 (SEQ ID No 10), and R12C6 (SEQ ID No 11) were aptamers identified at SELEX R12. R18C1 (SEQ ID No 12) and R1802 (SEQ ID No 13) were aptamers identified at SELEX R18. The gaps in the alignment of the nucleotides are represented by dashes (-) whereas the nucleotides are represented by A, T, C, and G.

FIG. 7 E2 binding capability of R18C1 LBD (SEQ ID No 12). The control (Ctrl) membranes included the E2 serial dilutions but not incubated with biotin-labelled LBD of R18C1 aptamer. The EtOH membranes included EtOH treated with biotin-LBD of R18C1 aptamer but no E2.

FIG. 11 Nucleotide alignment of BPA LBD. LBD nucleotides of BPA-01 (SEQ ID No 14), BPA-04 (SEQ ID No 15) and BPA-10 (SEQ ID No 16) isolated from basic, counter selection, and surfactant SELEX respectively were subjected to nucleotide alignment. The gaps in the alignment of the nucleotides are represented by dashes (-) whereas the nucleotides are represented by A, T, C, and G.

FIG. 12 BPA binding capability of BPA-04 LBD (SEQ ID No 15). The control (Ctrl) membranes include the BPA serial dilutions but are not incubated with biotin-labelled LBD of BPA-04 aptamer. The ethanol membranes include ethanol treated with biotin-LBD of BPA-04 aptamer but no BPA.

DETAILED DESCRIPTION

Definitions

Figure 1:
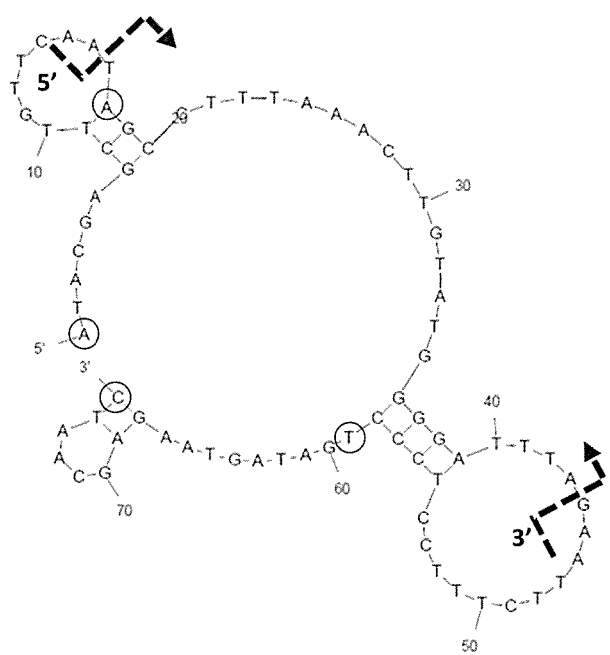
FIG. 1 The predicted 2D structure of R12C1 (SEQ ID No 1) using mFold. The 5' and 3' refer to the ends of the aptamer whereas the numbers (i.e. 10, 20 etc.) refer to the nucleotide positions within the 75 nucleotide sequence. The forward primer nucleotides are start from, and finish at the two light grey highlighted A's. The reverse primer nucleotides start from the darker grey highlighted T and finishes at the C. The nucleotides involved in the LBD are marked inside the dashed lines with the arrow pointing to the 5' to 3' direction.

As used in the specification and the appended claims, the singular forms "a," "an" and "the" include plural referents unless the context clearly dictates otherwise. And unless the context clearly requires otherwise, throughout the description and the claims, the words "comprise", "comprising" and the like, are to be construed in an inclusive sense as opposed to an exclusive or exhaustive sense, that is to say, in the sense of "including, but not limited to".

The term "aptamer" or "nucleic acid aptamer" means single stranded DNA sequence (ssDNA) or RNA sequence.

The term "nuclease" refers to is an enzyme that is capable of cleaving a phosphodiester bond between the nucleotide subunits of nucleic acids. Suitable nuclease enzymes would be readily known by those of skill in the art. Examples of nucleases include but are not limited to 5' exonucleases comprising Lambda exonuclease, T7 Exonuclease, and RecJ$_f$; suitable 3' exonucleases include but are not limited to Exonuclease T, and Exonuclease I. Suitable examples may be found at https://www.neb.com/tools-and-resources/selection-charts/properties-of-exonucleases-and-endonucleases.

The term "N40 random" is intended to mean the portion of an aptamer where the nucleotide sequence is randomly organised. The randomly organised nucleotides provide diversity necessary for the SELEX processes. The numerical number represents the number of nucleotides involved in the random region and can be any length as preferred by aptamer design.

The term "substrate" is intended to mean a target substrate, molecule, protein, antibody that a nucleic acid aptamer sequence has an affinity for.

Abbreviations

BWB Binding and washing buffer to stabilise aptamer
  2 mM TRIS-HCL, pH 7.5 containing 10 mM NaCl, 0.5 mM KCl, 0.2 mM
  MgCl$_2$, 5% v/v EtOH, 1% v/v IGEPAL® non-ionic surfactant DNAse Deoxyribonuclease
dNTPs Purchased from Life Technologies Catalog number: 10297-018
EB Elution buffer Qaigen mini elute kit Cat #28006. 10 mM Tris-Cl, pH 8.5
E2 Ethynylestradiol
g gravity
LBD Ligand binding domain
NE buffer 1 10 mM Bis-Tris-Propane-HCl, 10 mM MgCl$_2$, 1 mM DTT, pH 7.0 @ 25° C.
NE buffer 2 New England BioLabs Buffer 2 Cat #B7002S
  50 mM NaCl, 10 mM Tris-HCl, 10 mM MgCl$_2$, 1 mM DTT, pH 7.9 @ 25° C.
P1 Buffer Qaigen mini elute kit Cat #28006
  50 mM Tris-HCl, pH 8.0, 10 mM EDTA, 100 µg/ml RNaseA
Neutralisatio Qaigen mini elute kit Cat #28006
n Buffer N3 4.2 M Gu-HCl, 0.9 M potassium acetate, pH 4.8
P2 Buffer Qaigen mini elute kit Cat #28006.
  200 mM NaOH, 1% SDS
PB buffer Qaigen mini elute kit Cat #28006.
  5M Gu-HCl, 30% isopropanol
PE buffer Qaigen mini elute kit Cat #28006.
  10 mM Tris-HCl, pH 7.5, 80% ethanol
SL stem and loop
TAE tris acetate EDTA
TdT terminal transferase purchased from New England Biolabs Cat #M0315L Discussion The present inventor has surprisingly and advantageously developed methodology for identifying the LBD in nucleic acid aptamer sequences particularly those that interact with desirable substrate targets.

The use of enzymes to identify LBDs in aptamer sequences has not been shown before and provides the benefit of being less resource demanding when compared to existing techniques such as DNA foot printing, X-ray crystallography or NMR.

The method of the present invention works by incubating a nucleic acid aptamer sequence with a target substrate to which the aptamer is capable of binding. The bound aptamer target substrate combination is then incubated with a digestive enzyme (preferably an exonuclease). The digestive enzymes (5' and 3' enzymes) are selected for use in the current method based on the ability of the enzyme to freely digest available non-associating nucleotides i.e. nucleotides that do not form a binding association or interaction with the target substrate. The nucleotide sequences associated with binding the target substrate, or interacting with the target substrates remain intact and undigested, providing a unique nucleic acid aptamer sequence (also referred to as the LBD) that identifies the key nucleotide sequences required for binding the target substrate.

The present inventor has also shown that incubation of the aptamer and target substrate before enzymatic digestion is important for reproducibility of the digestion procedure. Without wishing to be bound by theory, the present inventor postulates that long incubation times for binding the aptamer and the target substrate (i.e. up to about 18 hours but preferably about 4 hr.) are preferred because of the highly flexible properties of aptamers and the optimal time required for the aptamer to associate with the target substrate. This is also dependent on the binding kinetics of the aptamer molecule and the conditions of necessary for the optimal binding. Therefore, longer time is required for the polynucleotide sequence (aptamer) to undergo the sequential folding combinations before achieving the lowest energy conformation during interaction with the target substrate.

In addition, the linearisation of the aptamer by heat denaturation and subsequent chilling on ice prior to co-incubation with the target substrate may also impact upon the time required to evolve into the appropriate conformation. It is common general knowledge in the field, that heat denaturing an aptamer results in linearisation of the aptamer. Chilling the aptamer on ice holds the linearised aptamer conformation for a longer period of time and prevents self-folding, therefore exposing most if not all the nucleotide bases to the target substrate allowing efficient interaction with the target substrate. It is preferential to use heat denaturation prior to enzymatic digestion as it is likely that other forms of denaturation of the aptamer will affect the aptamer-target substrate association interaction. However, the step of denaturisation can be avoided or overcome by incubating the aptamer with the target ligand for a longer period of time than is required compared to when heat denaturisation is performed.

The target substrate solutions were prepared using the aptamer binding buffer (BWB) containing 5% (v/v) ethanol. The inclusion of a water miscible organic solvent, such as ethanol, was considered an important consideration for optimal and consistent aptamer interactions with the target substrate. It is believed that the water miscible organic solvent assists in retaining solubility of the target substrate in the aqueous buffer solution. Those of skill in the art will realise that any organic solvent that provides the desired feature of assisting the solubility of the target substrate into water, without causing precipitation of the polynucleotide sequence may be used.

The 3' and/or 5' terminal specific activity of the exonucleases (i.e. 5' and 3' exonuclease) can be tested with or without incorporating biotin at the respective terminals of the aptamer while evaluating the conditions for optimal enzyme activity. The biotin is used to establish whether the nucleases were specific or not to freely available nucleotides because 5' and 3' enzymes are unable to digest biotin labelled aptamers whereas the unlabelled aptamer is fully digested. Those of skill in the art will realise that any molecule that can be incorporated at the terminal end of the aptamer and has the ability to restrict the accessibility of the enzymes to the aptamer sequence can be used. Therefore, exonuclease enzymes used in this method are highly specific for the respective 3' and/or 5' terminals and appear to be unable to digest the aptamer unless the nucleotides are freely available. The specific activity of the enzyme to digest only unprotected nucleotides, as described herein, reiterates that exonucleases are only able to digest freely available nucleotides of the aptamer and the nucleotides involved in the formation of the overall 3D structure upon interaction with target substrates are not digested.

It is worth noting that the 5' and 3' exonuclease enzyme digestion is best carried out in discrete independent steps (i.e. in separate steps from each other) to avoid complications that may arise because of differences in the specific conditions required for optimal exonuclease enzyme activity whilst maintaining integrity of the aptamer-target substrate complex.

Following exonuclease treatment, the digested aptamer is precipitated using excess ethanol as a means to concentrate the aptamer for the subsequent treatment. A person of skill in the art will realise that any water miscible solvent may be used to precipitate the digested aptamer. The resulting product (the exonuclease truncated aptamer) is treated with terminal transferase enzyme to allow for the poly A tail to be added at the 3' end. Treating of the exonuclease truncated aptamer with a terminal transferase enzyme allows for PCR amplification of the truncated aptamer and its ligation into a plasmid vector system. However, treating with terminal transferase enzyme may not be necessary if the concentration of aptamer used for exonuclease truncation can be clearly visualised in gel electrophoresis using DNA staining methods. A person of skill in the art would realise that gel electrophoresis extraction of the fragments of interest, sequencing and/or ligation into a plasmid would also be suitable for use in the described method.

The 5' exonuclease enzyme digestion generates a "blunt" 5' end which restricts the subsequent manipulation prior to ligation into a plasmid vector system. After thorough investigation, asymmetric PCR using only the reverse primer and the truncated aptamer product generate a product resulting in efficient ligation into the plasmid vector system. As an added measure, the ligation reaction time is increased to improve on the reaction efficiency. Furthermore, simultaneous cleavage of aptamers are likely to further restrict the capability of the un-cleaved aptamer to be ligated into a plasmid based system for sequencing purposes.

TABLE 1

Aptamer Sequences Prior to enzymatic digestion.

| SEQ ID No | SEQ Name | Target | FULL SEQUENCE (prepared by SELEX) |
|---|---|---|---|
| 1 | R12C1 | E2 | 5'-ATACGAGCTTGTTCAATAGCCTTTAAACTTGTATGGGGATTTAGAATTCTTTCCTCCCTGATAGTAAGAGCAATC-3' |
| 2 | R12C3 | E2 | 5'-ATACGAGCGTTCAATATAGTAGAGATTCACATTTGTGCCTATGATCTATTTCCGGATGATAGTAAGAGCAATC-3' |
| 3 | R12C6 | E2 | 5'-ATACGAGCTTGTTCAATATGTGCATGTTTTTTTGTTTGATCATCACTTTCCCTTTACTTGATAGTAAGAGCAATC-3' |
| 4 | R18C1 | E2 | 5'-ATACGAGCTTGTTCAATACGAAGGGATGCCGTTTGGGCCCAAGTTCGGCATAGTGTGGTGATAGTAAGAGCAATC-3' |
| 5 | R18C2 | E2 | 5'-ATACGAGCTTGTTCAATACCGTACGGCGGCGGTCAGGGGCCAAAGTGAGTGTGGCTGGTGATAGTAAGAGCAATC-3' |
| 6 | BPA-01 | BPA | 5'-ATACGAGCTTGTTCAATATCGCCGGCGCCGGCCTAGTCTCAAAAAGGGCACTCCCCTGTGATAGTAAGAGCAATC-3' |
| 7 | BPA-04 | BPA | 5'-ATACGAGCTTGTTCAATACGTTCGGTTGTAAACTTGAGTCATGAGCCCGCTTCCCCGGTGATAGTAAGAGCAATC-3' |
| 8 | BPA-10 | BPA | 5'-ATACGAGCTTGTTCAATACAGTTCATTTCACCCTGAGAGTGGGCTAAGTTGGGCATAGTGATAGTAAGAGCAATC-3' |

TABLE 2

Ligand Binding domains identified by enzymatic digestion of sequences in Table 1.

| SEQ ID No | SEQ Name | Target | ENZYMATICALLY DIGESTED SEQUENCE |
|---|---|---|---|
| 9 | R12C1 | E2 | 5'-TAGCCTTTAAACTTGTATGGGGATTTA-3' |
| 10 | R12C3 | E2 | 5'-CATTTGTGCCTATGATCTATTTCCGGAT-3' |
| 11 | R12C6 | E2 | 5'-CAATATGTGCATGTTTTTTGTTTGAT-3' |
| 12 | R18C1 | E2 | 5'-GGGATGCCGTTTGGGCCCAAGTTCGGCATAGTGTGGTG-3' |
| 13 | R18C2 | E2 | 5'-GGTGAGGGGCCAAAGTGAGTGTGGCTGG-3' |
| 14 | BPA-01 | BPA | 5'-AAGGGCACTCCCCTGTGAT-3' |
| 15 | BPA-04 | BPA | 5'-TCATGAGCCCGCTTCCCC-3' |
| 16 | BPA-10 | BPA | 5'-TACAGTTCATTTCACCCTGAGAGTGGGCT-3' |

Five ssDNA aptamers (R12C1 (SEQ ID No 1), R1203 (SEQ ID No 2) and R12C6 (SEQ ID No 3) and R18C1 (SEQ ID No 4) and R1802 (SEQ ID No 5)) capable of binding E2 with various sensitivities have been shown to be effective in exonuclease digestion to identify the LBD. Interestingly, the present inventors have established that the LBD of aptamers that are capable of binding E2 comprise between 27 and 38 nucleotides, despite differences in the nucleotide composition and the number of SELEX rounds undertaken before isolation (i.e. R12 and R18). It is believed that with greater number of SELEX rounds, the aptamers sensitivity and specificity to the target molecule is improved.

Enzymatic digestion of the R12C1 (SEQ ID No 1) aptamer produces a 27 nucleotide LBD (SEQ ID No 9) (FIG. 1). The first two nucleotides (i.e. 17th and $18^{th}$ nucleotides) of SEQ ID No 9 are contributed from the forward primer region nucleotides. However, the majority of the nucleotides of the SEQ ID No 9 are found in the N40 random region of SEQ ID No 1. The E2 LBD (SEQ ID No 9) can be located on the predicted 2D structure (FIG. 1) and are identified as being partially involved in the formation of two SL structures (17th to 20th and 36th to $43^{rd}$ nucleotides of SEQ ID No 1). The remainder of the nucleotides (i.e. 21st to $35^{th}$ nucleotides of SEQ ID No 1) are involved in linking the two SL structures.

Figure 2:
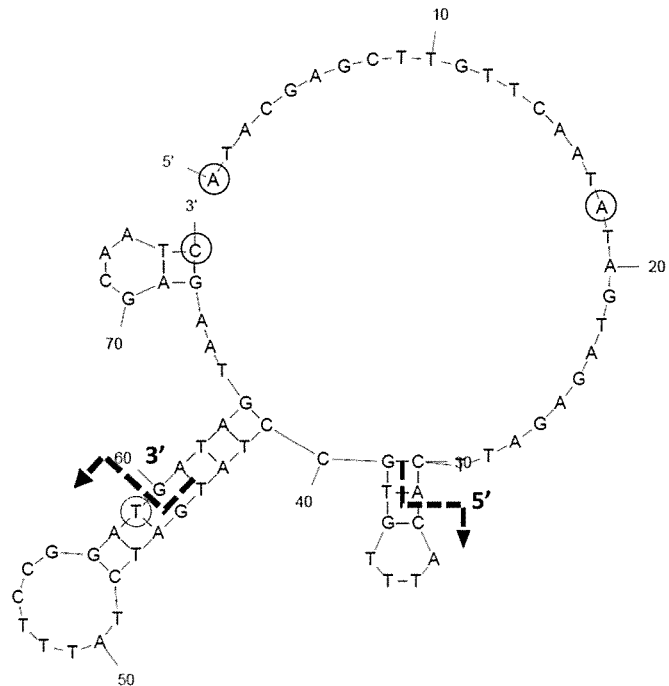
FIG. 2 The predicted 2D structure of R12C3 (SEQ ID No 2) using mFold. The 5' and 3' refer to the ends of the aptamer whereas the numbers (i.e. 10, 20 etc.) refer to the nucleotide positions within the 75 nucleotide sequence. The forward primer nucleotides are start from, and finish at the two light grey highlighted A's. The reverse primer nucleotides start from the darker grey highlighted T and finishes at the C. The nucleotides involved in the LBD are marked inside the dashed lines with the arrow pointing to the 5' to 3' direction.
Figure 3:
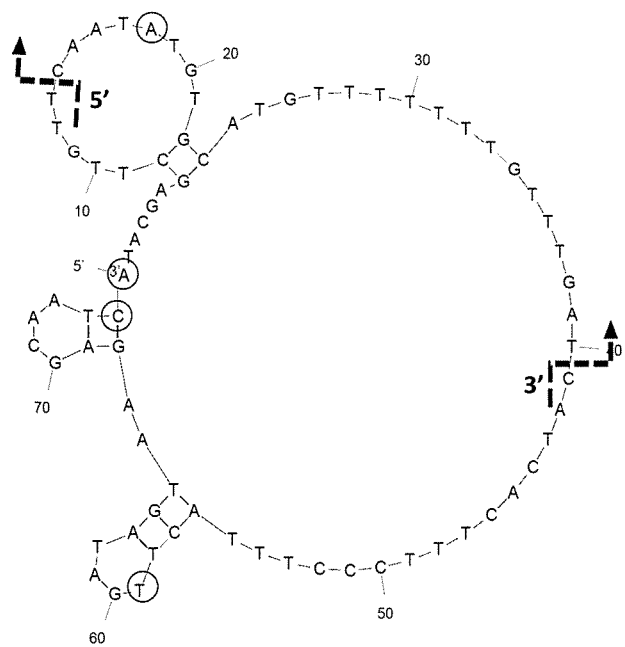
FIG. 3 The predicted 2D structure of R12C6 (SEQ ID No 3) using mFold. The 5' and 3' refer to the ends of the aptamer whereas the numbers (i.e. 10, 20 etc.) refer to the nucleotide positions within the 75 nucleotide sequence. The forward primer nucleotides are start from, and finish at the two light grey highlighted A's. The reverse primer nucleotides start from the darker grey highlighted T and finishes at the C. The nucleotides involved in the LBD are marked inside the dashed lines with the arrow pointing to the 5' to 3' direction.

Similarly, enzymatic digestion of R12C3 (SEQ ID No 2) produces a 28 nucleotide LBD (SEQ ID No 10) (FIG. 2). Most of the nucleotides of SEQ ID No 10 are also contributed by the N40 random region of SEQ ID No 2 (32nd to $58^{th}$ nucleotides of SEQ ID No 2). However, the nucleotide at the 59th position of SEQ ID No 2 forms part of the reverse primer region of the aptamer (FIG. 2). The E2 LBD (SEQ ID No 10) nucleotides can also be located on the predicted 2D structure (FIG. 2) and these are identified as being partially involved in the formation of two SL structures (32nd to 39th and 41st to 59th SEQ ID No 2). However, only one nucleotide ($40^{th}$ nucleotide of SEQ ID No 2) is involved in linking the two SL structures. R12C6 (SEQ ID No 3) enzymatic digestion also produces a 27 nucleotide E2 LBD (SEQ ID No 11) (FIG. 3). The LBD (SEQ ID No 11) comprises of nucleotides from the forward primer (14th to 18th of SEQ ID No 3) and N40 random region of SEQ ID No 3(19th to 40th SEQ ID No 3). The E2 LBD nucleotides of R12C6 (SEQ ID No 3) are also located on the predicted 2D structure (FIG. 3) and are identified as being somewhat involved in the formation of one of the SL structure (14th to 23rd nucleotides of SEQ ID No 3). The nucleotides (24th to 40th nucleotides of SEQ ID No 3) arise from the region between two SL structures.

Figure 4:
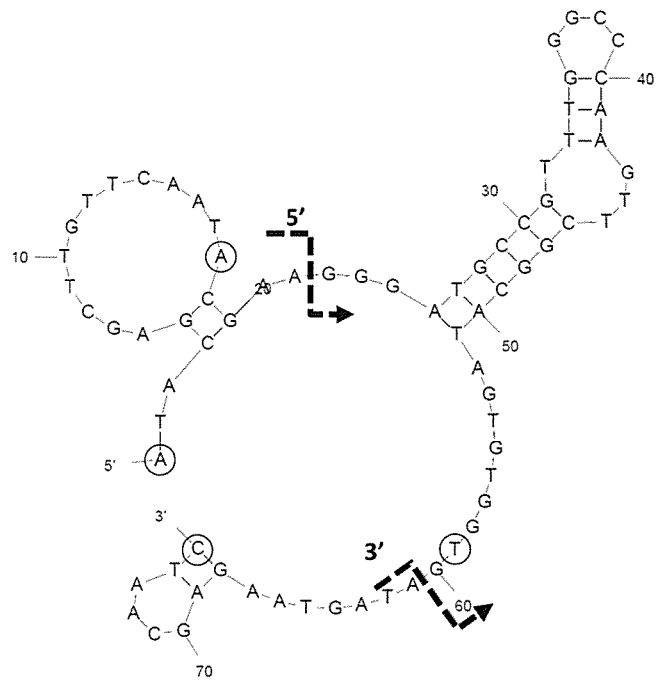
FIG. 4 The predicted 2D structure of R18C1 (SEQ ID No 4) using mFold. The 5' and 3' refer to the ends of the aptamer whereas the numbers (i.e. 10, 20 etc.) refer to the nucleotide positions within the 75 nucleotide sequence. The forward primer nucleotides are start from, and finish at the two light grey highlighted A's. The reverse primer nucleotides start from the darker grey highlighted T and finishes at the C. The nucleotides involved in the LBD are marked inside the dashed lines with the arrow pointing to the 5' to 3' direction.

Enzymatic digestion of R18C1 (SEQ ID No 4) produces a 38 nucleotide E2 LBD (SEQ ID No 12) and can be seen in the predicted 2D structure (FIG. 4). The LBD (SEQ ID No 12) comprises nucleotides from the N40 random (i.e. $23^{rd}$ to 60th nucleotides of SEQ ID No 4) and the reverse primer region (59th and 60th nucleotides of SEQ ID No 4). Additionally, these nucleotides are also identified as being partially involved in the formation of one of the SL structure (32nd to 51st nucleotides of SEQ ID No 4) while the 52nd to 60th nucleotides of SEQ ID No 4 are from the region between two SL structures.

Figure 5:
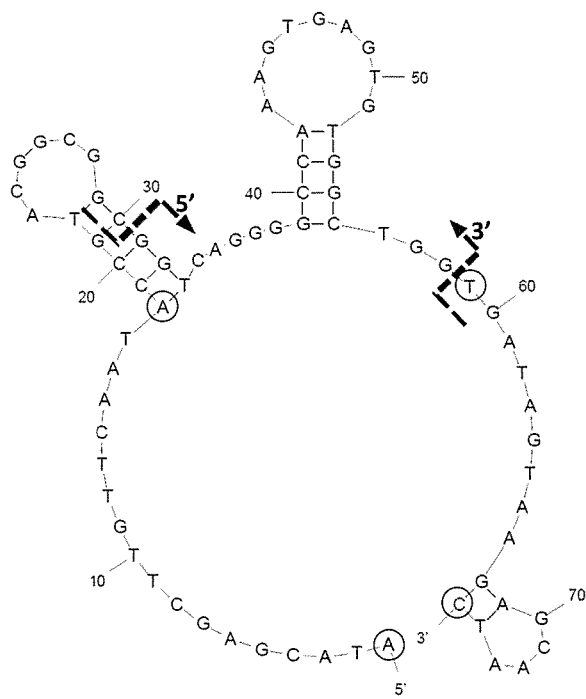
FIG. 5 The predicted 2D structure of R18C2 (SEQ ID No 5) using mFold. The 5' and 3' refer to the ends of the aptamer whereas the numbers (i.e. 10, 20 etc.) refer to the nucleotide positions within the 75 nucleotide sequence. The forward primer nucleotides are start from, and finish at the two light grey highlighted A's. The reverse primer nucleotides start from the darker grey highlighted T and finishes at the C. The nucleotides involved in the LBD are marked inside the dashed lines with the arrow pointing to the 5' to 3' direction.
Figure 8:
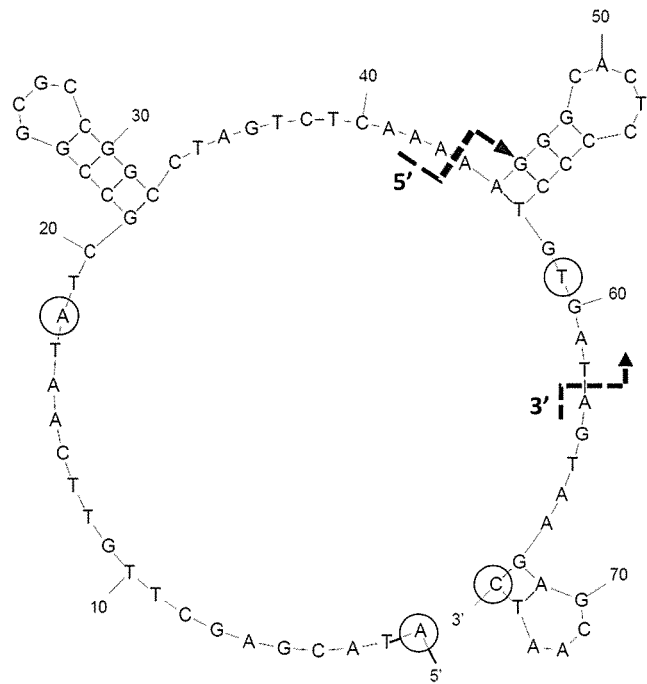
FIG. 8 The predicted 2D structure of BPA-01 (SEQ ID No 6) using mFold with the LBD. The 5' and 3' refer to the ends of the aptamer target substrate whereas the numbers (i.e. 10, 20 etc.) refer to the nucleotide positions within the 75 nucleotide sequence. The forward primer nucleotides are start from, and finish at the two light grey highlighted A's. The reverse primer nucleotides start from the darker grey highlighted T and finishes at the C. The nucleotides involved in the LBD are marked inside the dashed lines with the arrow pointing to the 5' to 3' direction.

For aptamer R18C2 (SEQ ID No 5), 28 nucleotide E2 LBD (SEQ ID No 13) can be identified from enzymatic digestion (FIG. 5). The LBD (SEQ ID No 13) comprises nucleotides exclusively from the N40 random region of SEQ ID No 5 (31st to $58^{th}$ nucleotides). The E2 LBD (SEQ ID No 13) nucleotides can also be seen in the predicted 2D structure (FIG. 5). These nucleotides are also partially involved in the formation of one partial (31st to 33rd nucleotides of SEQ ID No 5) and one complete SL structure (39th to 55th nucleotides of SEQ ID No 5). The two regions flanking the SL structures are also part of SEQ ID No 13(i.e. 34th to 38th and 56th to 58th nucleotides of SEQ ID No 5).

Alignment of the LBDs of the aptamers capable of binding E2 identifies possible homologous nucleotide sequences which are summarised in FIG. 6. Alignment of nucleotides reveals some regions with conserved sequences. For example, for SELEX R12, there are 8 shared nucleotides for the three aptamers (R12C1 (SEQ ID No 9), R12C3 (SEQ ID No 10), and R1206 (SEQ ID No 11)): R12C1 (SEQ ID No 9) and R12CC3 (SEQ ID No 10) share 15 common nucleotides; and, R1203 (SEQ ID No 10) and R12C6 (SEQ ID No 11) share 16 nucleotides. For the R18 aptamers, 17 nucleotides (R18C1 (SEQ ID No 12) and R18C2 (SEQ ID No 13)) are shared between the two aptamers.

Alignment of the LBD nucleotides from the monoclonal aptamers show a high degree of conservation. In particular, aptamers R12C1 (SEQ ID No 9), R1203 (SEQ ID No 10), and R12C6 (SEQ ID No 11) show a high degree of homology in the nucleotide sequences (FIG. 6).

Without wishing to be bound by theory, it is thought that the similar numbers for the LBD could be due to the high degree of nucleotide conservation among the aptamers that are identified for binding to E2 from the same initial pool. Analyses of the LBD nucleotides also revealed that there was some binding contribution from the forward and reverse primer regions.

It is also evident in some aptamers that the diversity of nucleotides in the N40 random region may influence a number of nucleotides from the constant regions (forward and reverse primers) that are involved in the formation of the specific 3D structure when bound to the target substrate. Therefore, disregarding the role of the constant regions in the secondary structure may not in itself, always be beneficial during aptamer refinement.

The enzymatic digestion methodology was also applied to sequences known to have some affinity for BPA (SEQ ID Nos: 6, 7 and 8) to provide LBD aptamers, BPA-01 (SEQ ID No 14), BPA-04 (SEQ ID No 15) and BPA-10 (SEQ ID No 16), (FIGS. 8 to 12).

Enzymatic digestion of BPA-01 (SEQ ID No 6) produces a 19 nucleotide BPA-LBD (SEQ ID No 14). SEQ ID No 14 comprises of nucleotides from the N40 random (nucleotides 44th to 58th) and the reverse primer (59th to 62nd nucleotides) region of SEQ ID No 6. SEQ ID No 14 was also located on the predicted 2D structure (FIG. 8) and is identified to be involved in the formation of one complete SL structure (43rd to 57th nucleotides of SEQ ID No 6). Two regions flanking the SL structures were also part of the LDB (i.e. 44th and 58th to 62nd nucleotides of SEQ ID No 6).

Figure 9:
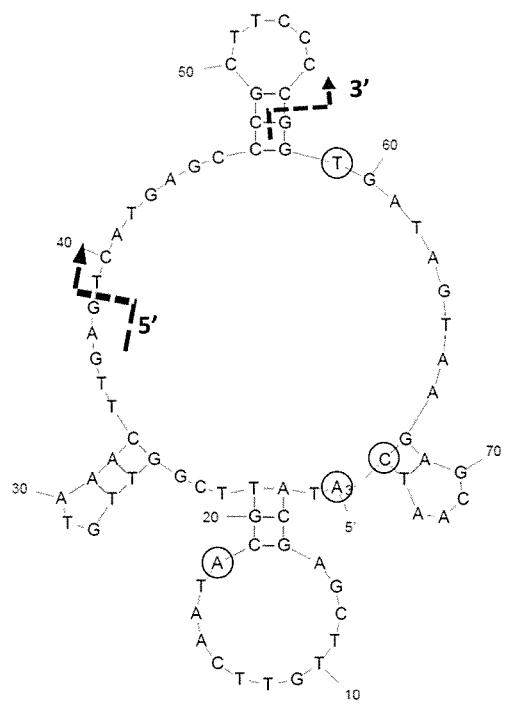
FIG. 9 The predicted 2D structure of BPA-04 (SEQ ID No 7) using mFold with the LBD. The 5' and 3' refer to the ends of the aptamer target substrate whereas the numbers (i.e. 10, 20 etc.) refer to the nucleotide positions within the 75 nucleotide sequence. The forward primer nucleotides are start from, and finish at the two light grey highlighted A's. The reverse primer nucleotides starts from the darker grey highlighted T and finishes at the C. The nucleotides involved in the LBD are marked inside the dashed lines with the arrow pointing to the 5' to 3' direction.

An 18 nucleotide LBD (SEQ ID No 15) results from enzymatic digestion of BPA-04 (SEQ ID No 7). SEQ ID No 15 comprises of nucleotides entirely from the N40 random region (44th to 56th nucleotides of SEQ ID No 7). Further, SEQ ID No 15 nucleotides are also located on the predicted 2D structure (FIG. 9). The LBD nucleotides (SEQ ID No 15) are additionally identified as being involved in the formation of one partial SL structure (47th to 56th nucleotides SEQ ID No 7) and one region flanking the SL structure (i.e. 39th to 46th nucleotides SEQ ID No 7).

Figure 10:
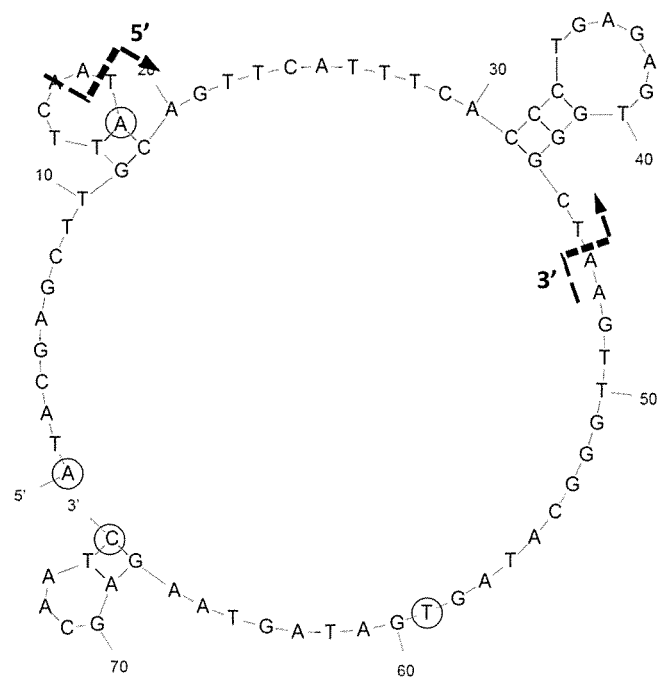
FIG. 10 The predicted 2D structure of BPA-10 (SEQ ID No 8) using mFold with the LBD. The 5' and 3' refer to the ends of the aptamer target substrate whereas the numbers (i.e. 10, 20 etc.) refer to the nucleotide positions within the 75 nucleotide sequence. The forward primer nucleotides are start from, and finish at the two light grey highlighted A's. The reverse primer nucleotides start from the darker grey highlighted T and finishes at the C. The nucleotides involved in the LBD are marked inside the dashed lines with the arrow pointing to the 5' to 3' direction.
Figure 13:
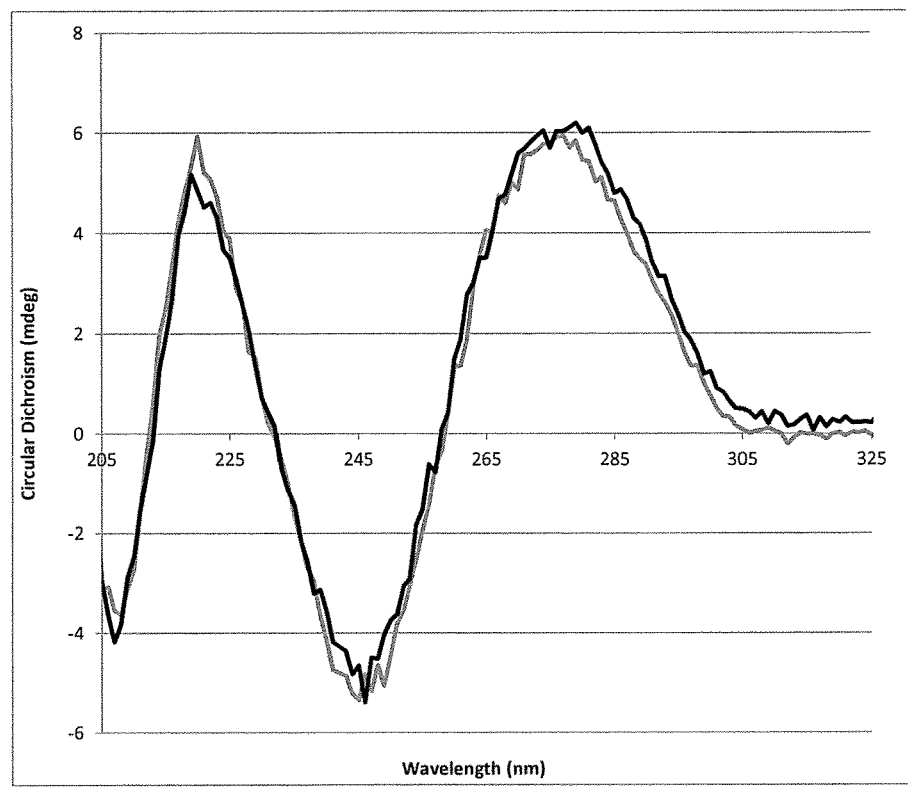
FIG. 13 Shows CD spectral analysis of R18C1 (SEQ ID No 4). Legend: Grey trace is aptamer only; black trace is aptamer +E2.

Enzymatic digestion of BPA-10 (SEQ ID No 8) produces a 22 nucleotide LBD (SEQ ID No 16). The LBD (SEQ ID No 16) comprises of nucleotides from the forward primer (nucleotides 17th and 18th) and N40 random region (nucleotides 19th to 38th of SEQ ID No 16) and are also located on the predicted 2D structure (FIG. 10). These nucleotides are also further identified to be involved in the formation of two partial SL structures (7th to 19th and 31st to 38th nucleotides of SEQ ID No 16) and one flanking region between the two SL structures (i.e. 20th to 30th nucleotides of SEQ ID No 16).

Alignment of nucleotides forming the LBD of the BPA aptamers (SEQ ID Nos 14, 15 and 16) showed that despite different SELEX methodologies being used, the nucleotide compositions contributing to the LBD between the BPA aptamers are similar. Both BPA-01 (SEQ ID No 14) and BPA-10 (SEQ ID No 16) share the nucleotide series of 'CCCTG' towards the 3' end indicating a high degree of conservation. In addition, all three aptamers (i.e. BPA-01 (SEQ ID No 14), BPA-04 (SEQ ID No 15), and BPA-10 (SEQ ID No 16)) share a triplicate of C nucleotides in a series (Table 2, FIG. 11).

Circular dichroism (CD) spectroscopy is applied in order to investigate conformational changes of the aptamers and to ascertain whether the aptamers are changing conformation between an unbound state and when bound with the target molecule (FIGS. 13 to 16). CD spectroscopy is a technique where the CD of molecules is measured over a range of wavelengths and allows the identification of changes in the aptamer structures in specific conditions.

Upon introduction of E2 to SEQ ID No 4, a reduction in the maximum absorbance peak is observed between 215 to 225 nm wavelengths. However, an increase in the maximum absorbance is also observed between 255 to 305 nm wavelengths. The change in the maximum absorption and the shift (275 to 305 nm) in the spectrum towards 305 nm show that there is a change in conformation of the aptamer upon introduction of E2 (FIG. 13), implying that the aptamers are flexible in their structure.

Figure 14:
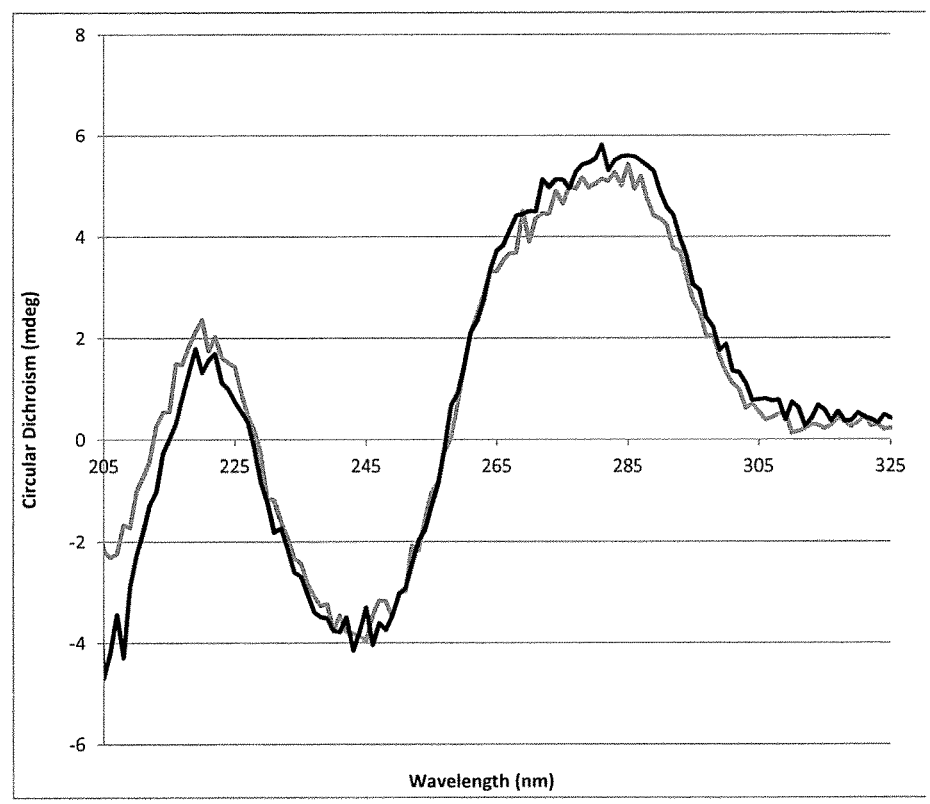
FIG. 14 shows CD spectral analysis of digested R18C1 (SEQ ID No 12). Legend: Grey trace is aptamer only; black trace is aptamer +E2.

A similar pattern to SEQ ID No 4 is observed for SEQ ID No 12, when E2 is introduced to the aptamer sample. A reduction at 215 to 225 nm and an increase (275 to 305 nm) in the maximum peak absorbance are observed. Furthermore, a positive millidegrees value is observed from 305 nm onwards and showed a change in conformation of the aptamer when it is exposed to the target substrate (FIG. 14). Therefore it can be concluded that both SEQ ID No 4 and SEQ ID No 12 demonstrate binding to E2. In addition, the aptamer sequence undergoes significant structural changes upon successfully binding to E2.

Figure 15:
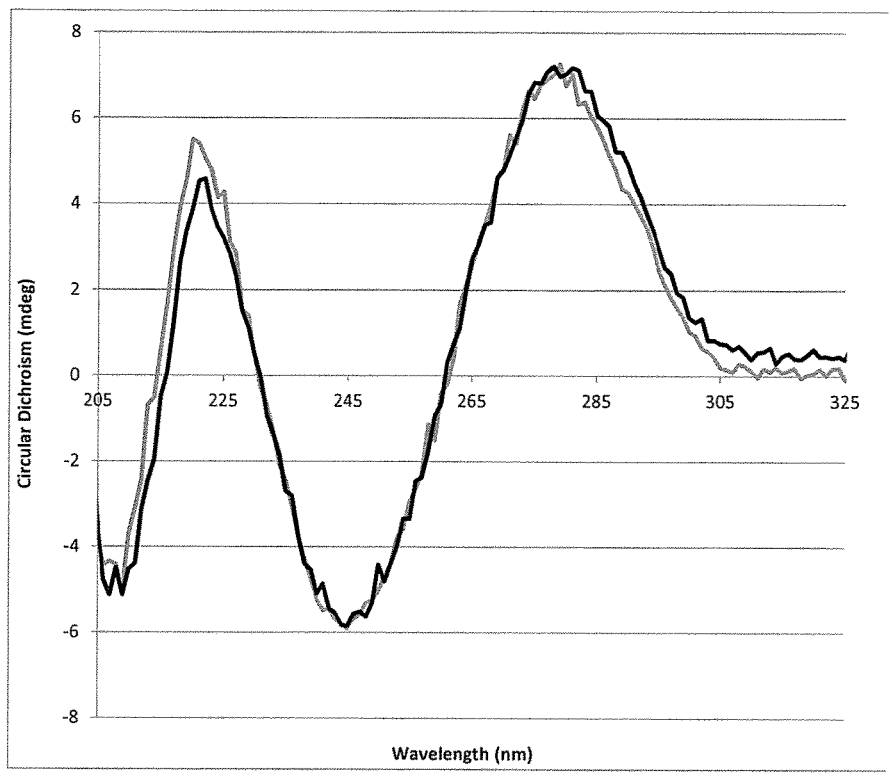
FIG. 15 shows CD spectral analysis of BPA-10 (SEQ ID No 8). Legend: Grey trace is aptamer only; black trace is aptamer +E2.

SEQ ID No 9 shows subtle differences between the absence of BPA and the presence of 10 µM BPA. A reduction in maximum absorption is observed around 215 to 225 nm wavelength. However, no significant increase in the maximum absorption is observed between 260 to 305 nm. A shift towards right hand-side is observed in the spectrum from 275 to 305 nm. The initial drop in absorption together with the change is shift indicated that structural changes are adopted upon introduction of BPA (FIG. 15).

Figure 16:
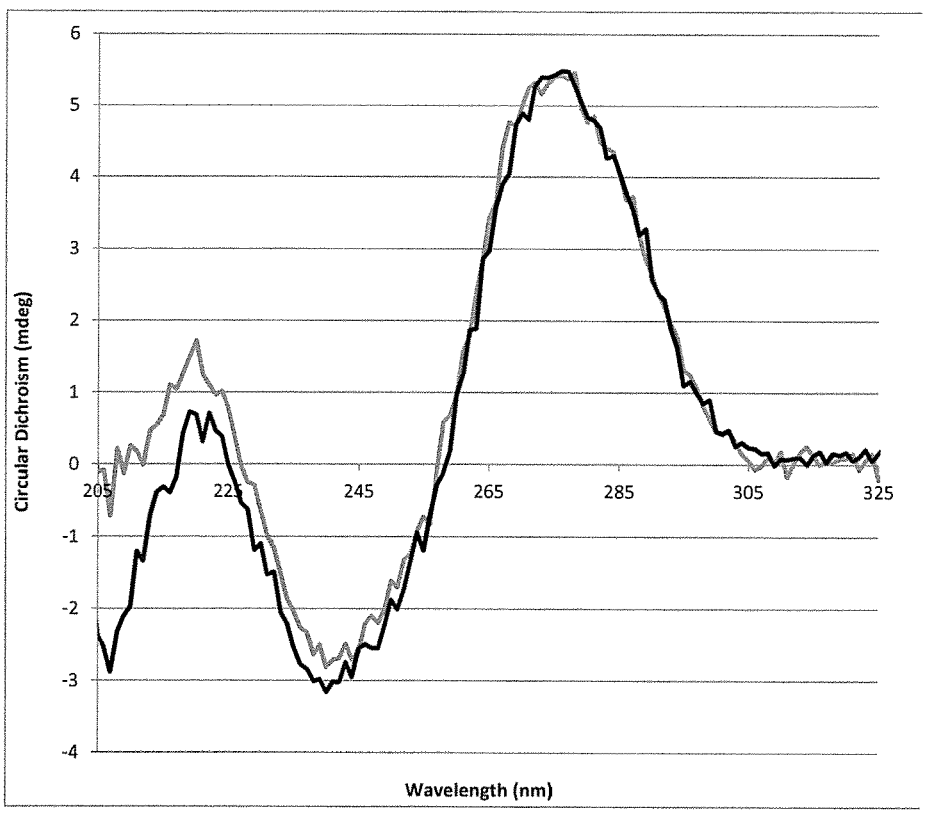
FIG. 16 shows CD spectral analysis of digested BPA-10 (SEQ ID No 16). Legend: Grey trace is aptamer only; black trace is aptamer +E2.

Upon introduction of BPA to SEQ ID No 16, a significant reduction in the maximum absorbance between 205 to 245 nm is observed. This change in the spectrum showed that significant structural changes are adopted by SEQ ID No 16 when BPA is introduced. Unlike the 75mer, no shift in the spectrum is observed (FIG. 16). SEQ ID No 9 and SEQ ID No 16 showed minor structural changes when BPA was introduced. The minor structural changes could be due to the mode of binding between the two aptamers and BPA. However, it can successfully be concluded that some structural changes was observed upon introduction of BPA.

Although this invention has been described by way of example and with reference to possible embodiments of any one of the aspects of the inventions thereof, it is to be understood that modifications or improvements may be made thereto without departing from the scope of the invention. The invention may also be said broadly to consist in the parts, elements and features referred to or indicated in the specification of the application, individually or collectively, in any or all combinations of two or more of said parts, elements or features. Furthermore, where reference has been made to specific components or integers of the invention having known equivalents, then such equivalents are herein incorporated as if individually set forth.

Any discussion of the prior art throughout the specification should in no way be considered as an admission that such prior art is widely known or forms part of common general knowledge in the field.

EXAMPLES

General Procedure for Aptamer Preparation by SELEX

A library containing a random pool of aptamer was subjected to affinity based selection process. An affinity column was used to screen for aptamers capable of associating with the target substrate with some affinity. Subsequently the aptamers with some affinity for the target substrate were isolated, followed by PCR amplification with some mutation, to generate variants intended to improve the aptamer's target binding capability. The process of affinity based selection and mutagenesis amplification led to the enrichment of aptamers with high affinity to the target molecule. Thereafter, the pool of aptamers having increased affinity was sequenced and the target binding characteristics were determined.

General procedure for target substrate preparation

100 µM solutions of the target substrate were prepared using 1×BWB with 5% (v/v) ethanol and were stored at 4° C. until required.

Generating Aptamers for 3' Exonuclease I digestion

PCR amplification utilising biotin was used to generate nucleic acid aptamers with a 5' biotin-label at the positive/leading strand end of the aptamer. The labelled nucleic acid aptamer was subjected to gel electrophoresis, followed by extraction prior to generation of single-stranded biotin-labelled aptamers using strand separation methodology. However, aptamers prepared by methods commonly known in the art may also be used, including, for example aptamer2 produced by synthetic nucleotide production.

General Procedure for Generating Aptamers for 5' Exonuclease Digestion

Biotin-labelled reverse primers were used in the PCR to generate aptamers with a biotin label at the 3' end. The aptamer was subjected to gel electrophesis and extraction before generation of single-stranded aptamer by strand separation.

General Procedure for PCR

All PCR amplification of aptamer was undertaken using the HotMaster™ Taq kit and prepared to a final reaction volume of 50 µL. The reaction buffer was made from 10 µM dNTPs, 1.1 µM each of both the forward and reverse primer, 2.5 mM $Mg^{2+}$ in the 1× buffer and 2U/50 µL HotMaster™ Taq polymerase enzyme.

Primary Incubation

The ssDNA aptamers were heat denatured at 85° C. for 1 min before being cooled in ice for 10 min. 100 µL of target substrate solution was added to the aptamers to form a primary incubation solution) and incubated at room temperature, with agitation, using an orbital shaker at 1,000 rpm for about four hours.

General 3' Exonuclease I Digestion Procedure

Exonuclease I reaction buffer obtained from New England Biosciences (Cat #M0293L) was added to the primary incubation solution to give a final concentration of 1× to the aptamer and ligand incubation mixture followed by the addition of 20 units of exonuclease I enzyme. The reaction mixture was vortexed for 5 sec at 500 rpm and then centrifuged for 5 sec at 2,000×g prior to incubation for 30 min in a water bath at 37° C. Following incubation, the enzyme in the reaction mixture was heat denatured by further incubation of the solution in a water bath at 80° C. for 20 min.

General 5' Exonuclease Digestion 5' exonuclease digestion of ssDNA aptamers was carried out using $RecJ_f$ recombinant enzyme. NE buffer 2 was added to the aptamer-target substrate incubation mixture (first incubation solution) to give a final concentration of 1× followed by the addition of 30 units of $RecJ_f$ enzyme. The reaction mixture was vortexed for 5 sec at 500 rpm and then centrifuged for 5 sec at 2,000×g prior to incubation for 20 min in a water bath at 37° C. Following incubation, the enzyme in the reaction mixture was heat denatured by further incubation in a water bath at 65° C. for 20 min.

Nucleic Acid Aptamer Precipitation

The digested aptamer product was concentrated by precipitation with ethanol followed by rehydration. To one volume of sample was added three volumes of cold 100% ethanol and the solution immediately incubated in dry ice for 2 hr. The samples were pelleted by centrifugation at 14,000×g for 20 min at 4° C., the supernatant was carefully removed, and the pelleted aptamer was washed by adding 700 µL of cold 70% ethanol. The resulting solution was then vortexed for 30 sec at 1,000 rpm. A second centrifugation at 14,000×g for 20 min at 4° C. was carried out to further pellet the nucleic acid before discarding the supernatant. The aptamer pellets were air dried before being rehydrated using 10 µL of DNAse free water.

Terminal Transferase Reaction

Following rehydration of the 3' exonuclease I digested aptamer, a poly A tail was added at the 3' end of the aptamer to assist with PCR amplification and ligation into the plasmid vector. The reaction was undertaken as specified in the manufacturer's protocol.

The reaction mixture containing 150 ng of digested nucleic acid aptamer template and 25 mM $CoCl_2$, 1 mM dATP, and TdT reaction buffer (obtained in a commercially available kit from New England Biosciences) was prepared and incubated for 1 hr. in a water bath at 37° C. The reaction mixture was placed in ice and 2 µL of 0.2 M EDTA (pH 8.0) was added to the mixture before heat denaturing the enzyme by incubating for 20 min in a water bath at 75° C.

PCR Amplification of 3' Exonuclease Digested Product

Following the terminal transferase reaction, the digested aptamer was used as a template in the PCR amplification to generate ample product for subsequent ligation into a plasmid vector. A non-modified forward primer and a poly T reverse primer were used for the reaction using a standard PCR procedure. The PCR product was electrophoretically separated on a 4% (w/v) agarose gel and 25 bp DNA ladder.

Asymmetric PCR Amplification of 5' Exonuclease Digested Product

Exonuclease digestion from the 5' end of the ssDNA aptamer produced a blunt end that restricted the efficiency for ligation of the aptamer into a plasmid vector necessary for sequencing. The rehydrated digested aptamer product following DNA precipitation was used as the template. Asymmetric PCR using only the reverse primer was carried out. All other reagents used in the PCR and amplification cycles were according to the General Procedure. The resulting PCR product was precipitated using ethanol and then rehydrated in 10 µL of DNase free water.

Selection and Identification of Monoclonal Aptamer

10 µL of the rehydrated digested aptamer from the PCR was added to 2× ligation buffer, 50 ng of pGEM-Teasy cloning vector and 3 units of T4 DNA ligase to provide a final reaction volume of 24 µL that was kept on ice. To improve on the efficiency of the ligation, the reagents were mixed by pipetting and then incubated overnight at 4° C. The plasmids were then transformed into E. coli cells. The transformed cells were grown in 950 µL of Luria broth (LB) for 1 hr. before being centrifuged at 3,000×g for 5 min. The supernatant was discarded and the pellet re-suspended in 100 µL LB and thereafter plated aseptically onto LB agar plates containing 2% X-gal (50 µL) and 50 µg/ml ampicillin. After plating, the LB-pellet solution was allowed to soak into the plates for 2 hrs. at room temperature prior to overnight incubation at 37° C. Distinct white colonies containing the target aptamer were selected and incubated overnight at 37° C. with agitation in LB media containing 50 µg/ml ampicillin antibiotics. The cultured cells were then purified using a QIAprep spin kit according to the manufacturer's instructions. The 10 ml overnight cultures in 20 ml glass vials were centrifuged at 13,000×g for 10 min before removal of the supernatant. The pelleted bacterial cells were re-suspended in 250 µL of P1 buffer before transferring the suspension into 1.7 ml micro-centrifuge tubes. 250 µL of P2 buffer was then added and gently mixed by inverting the tubes a few times. The suspension was incubated at room temperature for 5 min to lyse the cells before addition of 350 µL of neutralisation buffer N3, and the suspension was mixed by inverting the tubes prior to centrifugation at 13,000×g for 10 min. The supernatant was carefully transferred into QIAprep spin columns and centrifuged for 1 min at 13,000×g. The flow through was discarded and the column was washed using 500 µL of PB buffer before precipitating the DNA by washing with 750 µL of PE buffer. The columns were further centrifuged at 13,000×g for 1 min to remove traces of ethanol in the column from the PE buffer. The collection tubes were discarded and the columns placed in 1.7 ml micro-centrifuge tubes. The DNA from the column matrix was eluted using 50 μL of EB which was carefully added directly to the column matrix and incubated at room temperature for 1 min prior to centrifugation at 13,000×g for 1 min. The column was discarded and the eluted samples were stored at −20° C. until use. Restriction enzymatic digestion was performed to ensure that the product (i.e. target aptamer) was ligated successfully into the plasmid before sequence analysis.

Circular Dichroism (CD) Spectral Analysis of Aptamers

The ssDNA aptamer was heat denatured by incubating at 85° C. for 5 mins and chilled on ice for further 15 mins. An incubation solution (1.1 mL) was prepared containing 100 μM ssDNA aptamer and 10 μM target substrate and incubated overnight at room temperature. Following overnight incubation, 1 mL of the incubation solution was pipetted into a quartz cuvette and scanned using a CD spectrometer (AppliedPhotophysics) from 200 to 400 nm (FIGS. 13 to 16).

INDUSTRIAL APPLICATION

The method of the present invention finds use in the identification of ligand binding domains having high selectivity for target substrates.

REFERENCES

Bock, L. C., L. C. Griffin, J. A. Latham, E. H. Vermaas and J. J. Toole (1992). "Selection of single-stranded DNA molecules that bind and inhibit human thrombin." Nature 355(6360): 564-566.

Jo, M., J.-Y. Ahn, J. Lee, S. Lee, S. W. Hong, J.-W. Yoo, J. Kang, P. Dua, D.-k. Lee and S. Hong (2011). "Development of single-stranded DNA aptamers for specific bisphenol A detection." Oligonucleotides 21(2): 85-91.

Kelly, J. A., J. Feigon and T. O. Yeates (1996). "Reconciliation of the X-ray and NMR structures of the thrombin-binding aptamer d(GGTTGGTGTGGTTGG)." Journal of Molecular Biology 256(3): 417-422.

Kim, Y. S. and M. B. Gu (2014). "Advances in aptamer screening and small molecule aptasensors." Advances in Biochemical Engineering/Biotechnology 140: 29-67.

Kim, Y. S., H. S. Jung, T. Matsuura, H. Y. Lee, T. Kawai and M. B. Gu (2007). "Electrochemical detection of 17β-estradiol using DNA aptamer immobilized gold electrode chip." Biosensors and Bioelectronics 22(11): 2525-2531.

Kulbachinsky, A. (2007). "Methods for selection of aptamers to protein targets." Biochemistry (Moscow) 72(13): 1505-1518.

Luo, X., M. McKeague, S. Pitre, M. Dumontier, J. Green, A. Golshani, M. C. Derosa and F. Dehne (2010). "Computational approaches toward the design of pools for the in vitro selection of complex aptamers." RNA 16(11): 2252-2262.

Marshall, K. A. and A. D. Ellington (2000). "In vitro selection of RNA aptamers." Methods in Enzymology 318: 19-214.

McKeague, M. and M. C. DeRosa (2012). "Challenges and opportunities for small molecule aptamer development." Journal of Nucleic Acids 2012: 20.

Mehta, J., E. Rouah-Martin, B. Van Dorst, B. Maes, W. Herrebout, M.-L. Scippo, F. Dardenne, R. Blust and J. Robbens (2012). "Selection and characterization of PCB-binding DNA aptamers." Analytical Chemistry 84(3): 1669-1676.

Ruigrok, V. J. B., M. Levisson, J. Hekelaar, H. Smidt, B. W. Dijkstra and J. van der Oost (2012). "Characterization of aptamer-protein complexes by X-ray crystallography and alternative approaches." International Journal of Molecular Sciences 13(8): 10537-10552.

Wang, T., J. A. Hoy, M. H. Lamm and M. Nilsen-Hamilton (2009). "Computational and experimental analyses converge to reveal a coherent yet malleable aptamer structure that controls chemical reactivity." Journal of the American Chemical Society 131(41): 14747-14755.

Zianni, M., K. Tessanne, M. Merighi, R. Laguna and F. R. Tabita (2006). "Identification of the DNA bases of a DNase I footprint by the use of dye primer sequencing on an automated capillary DNA analysis instrument." Journal of biomolecular techniques 17(2): 103-113.

Publication US 2011/0251088.
Granted patent U.S. Pat. No. 7,306,904.
Publication WO 2013025930.
Patent application U.S. Ser. No. 14/326,329.

The invention claimed is:

1. A method for determining the sequence composition of a ligand binding domain of an aptamer, the method comprising:
   i. incubating the aptamer with a target antigen to form an aptamer-antigen complex;
   ii. treating the aptamer-antigen complex with an exonuclease specific for a single stranded nucleic acid, wherein the treating is performed for a time and under conditions sufficient to digest any single stranded portion of the aptamer not bound to the antigen, wherein separate exonucleases having 5'-3' and 3'-5' activity are used to treat the aptamer-antigen complex and the separate exonucleases are used sequentially in different reactions;
   iii. dissociating the exonuclease treated aptamer-antigen complex to yield a nucleic acid containing the ligand binding domain; and
   iv. sequencing the nucleic acid to determine the sequence composition of the ligand binding domain.

2. The method according to claim 1, wherein the exonuclease is selected from the group consisting of Lambda Exonucleases, T7 Exonuclease, RecJf, Exonuclease I and Exonuclease T.

3. The method according to claim 1, wherein the aptamer is selected from single stranded deoxyribose nucleic acid (ssDNA) aptamers and ribose nucleic acid (RNA) aptamers.

4. The method according to claim 1, wherein the aptamer and the target antigen are incubated for about 2 minutes to about 18 hours.

5. The method according to claim 1, wherein the aptamer-antigen complex achieves the lowest energy binding conformation.

6. The method according to claim 1, wherein the aptamer-antigen complex is treated with the exonuclease for about 1 minute to about 2 hours.

7. The method according to claim 1, wherein the incubating step or the treating step is performed in an aqueous solution or an aqueous miscible solution.

8. The method according to claim 1, wherein the incubating step or the treating step is performed in a buffer solution.

9. The method according to claim 8, wherein the buffer solution comprises a water miscible organic solvent.

10. The method according to claim 9, wherein the water miscible solvent is selected from an alcoholic solvent, a ketone solvent, an ether, an amide, a sulfoxide, or a mixture thereof.

11. The method according to claim 10, wherein the water miscible organic solvent is selected from acetone, acetonitrile, dioxane, dimethylsulfoxide (DMSO), N,N-dimethylformamide (DMF) ethanol (EtOH), isopropyl alcohol (IPA), methanol (MeOH) and tetrahydrofuran (THF), or a mixture thereof.

12. The method according to claim 9, wherein the water miscible solvent is ethanol.

* * * * *

SEQUENCE LISTING

```
<160> NUMBER OF SEQ ID NOS: 16

<210> SEQ ID NO 1
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 1
atacgagctt gttcaatagc ctttaaactt gtatggggat ttagaattct ttcctccctg     60
atagtaagag caatc                                                      75

<210> SEQ ID NO 2
<211> LENGTH: 73
<212> TYPE: DNA
<213> ORGANISM: Artificial Sequence
<220> FEATURE:
<223> OTHER INFORMATION: Synthetic polynucleotide
```

<400> SEQUENCE: 2
atacgagcgt tcaatatagt agagattcac atttgtgcct atgatctatt tccggatgat    60
agtaagagca atc                                                      73

<210> SEQ ID NO 3
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 3
atacgagctt gttcaatatg tgcatgtttt tttgtttgat catcactttc cctttacttg    60
atagtaagag caatc                                                    75

<210> SEQ ID NO 4
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 4
atacgagctt gttcaatacg aagggatgcc gtttgggccc aagttcggca tagtgtggtg    60
atagtaagag caatc                                                    75

<210> SEQ ID NO 5
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 5
atacgagctt gttcaatacc gtacggcggc ggtcaggggc caaagtgagt gtggctggtg    60
atagtaagag caatc                                                    75

<210> SEQ ID NO 6
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 6
atacgagctt gttcaatatc gccggcgccg gcctagtctc aaaaagggca ctcccctgtg    60
atagtaagag caatc                                                    75

<210> SEQ ID NO 7
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 7
atacgagctt gttcaatacg ttcggttgta aacttgagtc atgagcccgc ttccccggtg    60
atagtaagag caatc                                                    75

<210> SEQ ID NO 8

```
<211> LENGTH: 75
<212> TYPE: DNA
<213> ORGANISM: Artificial Sequence
<220> FEATURE:
<223> OTHER INFORMATION: Synthetic polynucleotide

<400> SEQUENCE: 8
atacgagctt gttcaataca gttcatttca ccctgagagt gggctaagtt gggcatagtg      60
atagtaagag caatc                                                      75

<210> SEQ ID NO 9
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 9
tagcctttaa acttgtatgg ggattta                                         27

<210> SEQ ID NO 10
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 10
catttgtgcc tatgatctat ttccggat                                        28

<210> SEQ ID NO 11
<211> LENGTH: 27
<212> TYPE: DNA
<213> ORGANISM: Artificial Sequence
<220> FEATURE:
<223> OTHER INFORMATION: Synthetic polynucleotide

<400> SEQUENCE: 11
caatatgtgc atgttttttt gtttgat                                         27

<210> SEQ ID NO 12
<211> LENGTH: 38
<212> TYPE: DNA
<213> ORGANISM: Artificial Sequence
<220> FEATURE:
<223> OTHER INFORMATION: Synthetic polynucleotide

<400> SEQUENCE: 12
gggatgccgt ttgggcccaa gttcggcata gtgtggtg                             38

<210> SEQ ID NO 13
<211> LENGTH: 28
<212> TYPE: DNA
<213> ORGANISM: Artificial Sequence
<220> FEATURE:
<223> OTHER INFORMATION: Synthetic polynucleotide

<400> SEQUENCE: 13
ggtgaggggc caaagtgagt gtggctgg                                        28

<210> SEQ ID NO 14
<211> LENGTH: 19
<212> TYPE: DNA
<213> ORGANISM: Artificial Sequence
<220> FEATURE:
<223> OTHER INFORMATION: Synthetic polynucleotide
```

```
<400> SEQUENCE: 14
aagggcactc ccctgtgat                                                      19

<210> SEQ ID NO 15
<211> LENGTH: 18
<212> TYPE: DNA
<213> ORGANISM: Artificial Sequence
<220> FEATURE:
<223> OTHER INFORMATION: Synthetic polynucleotide

<400> SEQUENCE: 15
tcatgagccc gcttcccc                                                       18

<210> SEQ ID NO 16
<211> LENGTH: 29
<212> TYPE: DNA
<213> ORGANISM: Artificial Sequence
<220> FEATURE:
<223> OTHER INFORMATION: Synthetic polynucleotide

<400> SEQUENCE: 16
tacagttcat ttcaccctga gagtgggct                                           29
```